Jan. 18, 1966 H. C. SWIM Plant Pat. 2,589
CAMELLIA PLANT
Filed May 4, 1964
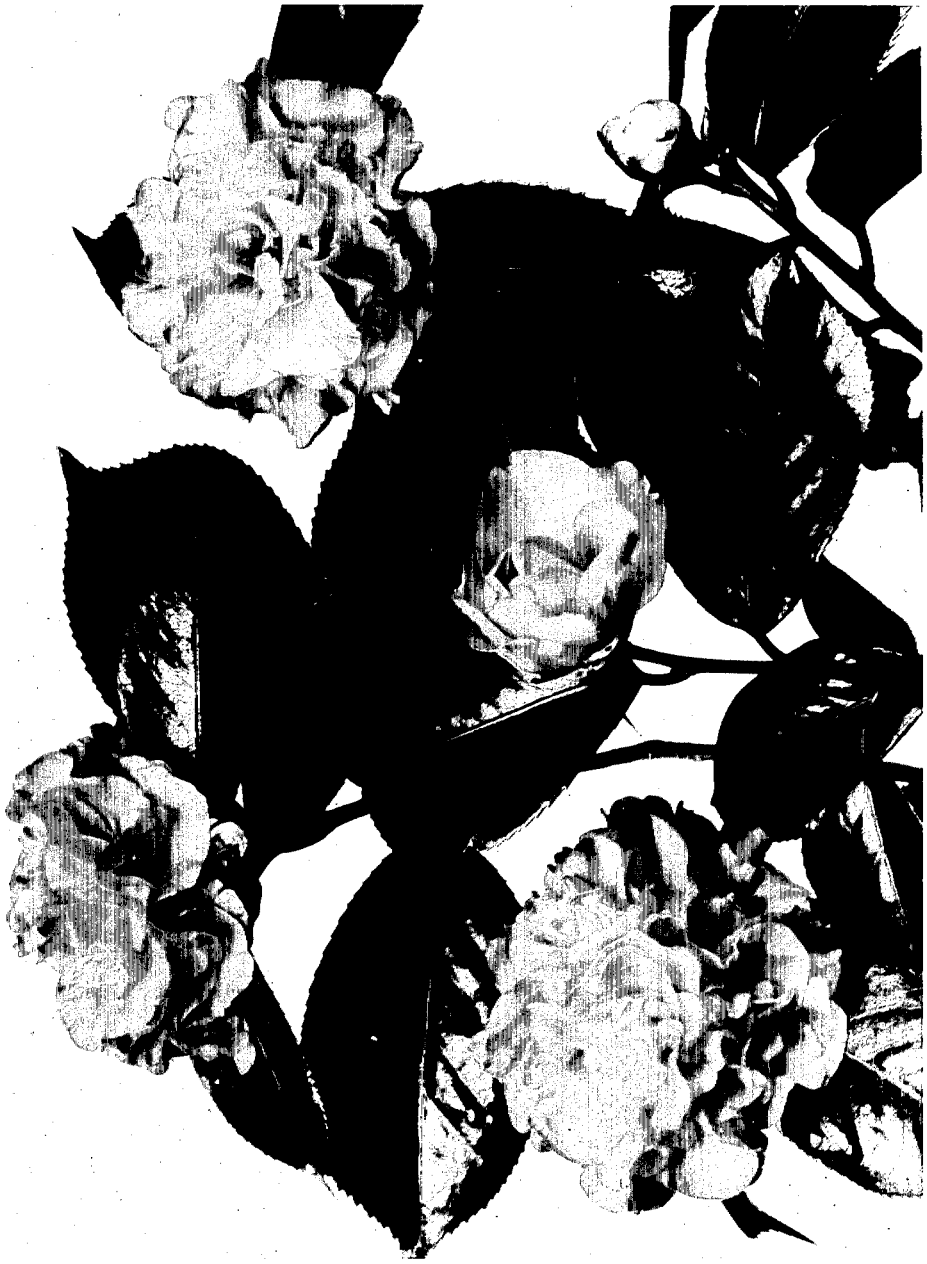
Inventor.
H. C. Swim
By: Robb & Robb
Attorneys.

United States Patent Office

Plant Pat. 2,589

Patented Jan. 18, 1966

2,589

CAMELLIA PLANT

Herbert C. Swim, Ontario, Calif., assignor to Armstrong Nurseries, Inc., Ontario, Calif., a corporation of California Filed May 4, 1964, Ser. No. 364,870
1 Claim. (Cl. Plt.—62)

The present invention relates to a new and distinct variety of camellia plant which was originated by me by crossing the variety known as "Anita" (unpatented) with the variety known as "Arejishi" (unpatented), the former being the seed parent and the latter being the pollen parent.

The general objective of this breeding was to produce a new and improved camellia variety in which there is combined certain desirable characteristics of both parent varieties, and particularly the vigorous and large-foliaged plant habit, bright red double flowers, and the early and long blooming season characteristics of the pollen parent "Arejishi," as well as the excellent, overall flowering and plant habits of the seed parent "Anita."

The parent variety "Anita" is best known for its fairly upright, moderately bushy plant habit, with leaves ranging from small to medium size, combined with a quite floriferous flower habit, said flowers ranging from 9 cm. to 12 cm. wide, being semi-double, with the petals arranged in a very formal manner and the flower color being generally white, but heavily marked with flecks and streaks of red, but with occasional sport branches bearing flowers of overall red color.

The pollen parent "Arejishi" is particularly characterized by a vigorous, upright-spreading, moderately branched plant habit, with large leaves having large and coarse marginal serrations, and bearing red flowers which are quite double and of medium size, ranging from 9 cm. to 11 cm. wide, and the flower form being between the anemone form and the peony form classification.

As the result of the foregoing breeding, my new camellia variety is endowed with the following unique combination of characteristics which are outstanding therein and which distinguish it from its parents, as well as from all other varieties of which I am aware:

(1) A vigorous, upright-spreading, rather moderately branched plant habit, with attractive, large, dark green foliage having large and coarse marginal serrations;

(2) Moderate floriferousness, with the flowers usually borne terminally, either singly or double and only occasionally laterally;

(3) Very attractive flowers of medium size and having from 25 to 35 petals, plus from 5 to 10 petaloids, with the open flowers being rather globular, and the petals being arranged in a graceful irregular manner usually covering most of the stamens and substantially corresponding to a camellia flower form classification identified as a full peony form;

(4) A distinctive and attractive bright Turkey Red flower color; and (5) A long blooming period ranging from late November or early December to April in southern California.

As compared with its seed parent "Anita," the leaves of my new camellia variety are considerably larger in size and have larger marginal serrations; the flowers are an irregular double and near peony form instead of being semi-double as in this parent; the flower color is red, whereas the flowers of this parent are white and only flecked and streaked with red; and the blooming period of my new variety is quite long, ranging from late November to early April, in contrast with the blooming period of this parent which ranges from late February to mid or late April.

In comparison with the pollen parent, "Arejishi," the leaves of my new variety are somewhat larger and proportionately wider; the flowers are of irregular double and near peony form in classification, whereas those of this parent fall more nearly intermediate the anemone and peony form classification; the flowers are slightly larger in size; and the blooming period of my new variety begins a few weeks later than that of this parent.

Asexual reproduction of my new variety by both grafting and cuttings, as performed at Ontario, California, shows that the foregoing characteristics and distinctions come true to form in my new camellia and are established and transmitted through succeeding propagations.

The accompanying drawing shows sypical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as (W)) and Robert Ridgeway's Color Standards and Nomenclature (hereinafter abbreviated as (R)) as indicated:

Type: Ornamental; flowering evergreen shrub; for general landscape use and for cut flowers.

Class: *Camellia japonica.*

Breeding: Seedling.

*Seed parent.*—"Anita."

*Pollen parent.*—"Arejishi."

Propagation: Holds its distinguishing characteristics through succeeding propagation by both grafting and cuttings.

*Plant*

Growth:

*Habit.*—Upright-spreading; moderately branched; somewhat open.

*Vigor.*—Very vigorous.

*New stems.*—Medium caliper; glabrous. Color—near Absinthe Green, Plate XXXI (R).

*Older stems.*—Glabrous; bark becomes fissured and scurfy. Color—between Russet, Plate XV (R) and Cinnamon-Brown, Plate XV (R).

*Mature branches.*—Rough and scurfy when a year or two old but becoming more smooth as original bark is sloughed off. Color—between Drab-Gray, Plate XLVI (R) and Light Grayish Olive, Plate XLVI (R).

Leaves:

*Habit.*—Moderately abundant.

*Texture.*—Thick; leathery.

*Size.*—Large. Width—from 7 to 8 cm. Length—from 11 to 13 cm.

*Petiole.*—Large caliper; from 11 to 13 mm. long; with shallow groove along upper surface; glabrous.

*Shape.*—From oval to obovate. Apex—variable but usually quite extended and acute. Base—varies from somewhat obtuse to somewhat acute. Margin—with large, coarse serrations; usually simply serrate but occasionally doubly serrate; and entire near petiole attachment.

*Upper surface.*—Glossy. Color—mature leaves—between Dark Dull Yellow-Green, Plate XXXII (R) and Empire Green, Plate XXXII (R), with main veins near Absinthe Green, Plate XXXI (R).

*Lower surface.*—Glossy. Color—mature leaves—near Absinthe Green, Plate XXXI (R), with veins near Empire Green, Plate XXXII (R).

*Flower*

Flowers borne: Sessile; mostly terminal, but a few axillary near end of shoot; usually single, but sometimes double when terminal.

Quantity of bloom: Moderate.

Time of bloom: One long season, usually from late November or early December to April at Ontario, California.

Fragrance: Mild but definite sweet fragrance.

Bud:

*Size (before calyx breaks).*—From medium to large size.

*Form (before calyx breaks).*—Usually ovoid.

*Sepals.*—Numerous, usually from 7 to 9 in number; increasing in size from the outermost which are nearly round, to the innermost which are broadly obovate; the two innermost sepals showing transition to petals with streaks of red petal tissue. Surface—pubescent; color—between Rainette Green, Plate XXXI (R) and Lime Green, Plate XXXI (R).

*Opening.*—Opens up well.

Bloom:

*Size (when fully open).*—Medium; averages from 9 cm. to 11 cm. in diameter.

*Petalage.*—Double; usually from 25 to 35 petals, often with 5 to 10 petaloids intermixed; often petals somewhat joined together for part of their length in varying manner.

*Form.*—Newly opened flower somewhat cupped, becoming high-centered and quite globular in full peony form, at maturity; the petals are gracefully but irregularly bunched, usually without anthers visible, and show waviness of margins and tendency to fold; variations in form, from time to time, show sometimes greater formal arrangement of petals, particularly toward the outer petals; sometimes a tight incurving of petal margins that gives a more rough flower form; sometimes occasional slight vegetative spotting and/or streaking at a few petal margins.

*Petals.* — Thickness — moderate. Surface—satiny, both inside and outside. Shape—somewhat irregular; petals usually broadly obovate to broadly oval or round; smaller petals to petaloids usually obovate or more narrow.

*Color.*—Newly opened flower: Outer petals—outside surface—near Turkey Red, Plate 721, page 94 (W) with veins near Currant Red, Plate 821/2, page 167 (W); inside surface—near Turkey Red, Plate 721, page 94 (W) with veins near Currant Red, Plate 821/2, page 167 (W). Inner petals—outside surface—near Turkey Red, Plate 721, page 94 (W) with veins near Currant Red, Plate 821/2, page 167 (W); inside surface—near Turkey Red, Plate 721, page 94 (W) with veins near Currant Red, Plate 821/2, page 167 (W). 2–3 days open flower: Outer petals—outside surface—between Turkey Red, Plate 721/1, page 94 (W) and Turkey Red, Plate 721/3, page 94 (W) with veins near Currant Red, Plate 821/3, page 167 (W); inside surface—between Turkey Red, Plate 721/1, page 94 (W) and Turkey Red, Plate 721/3, page 94 (W) with veins near Currant Red, Plate 821/3, page 167 (W). Inner petals—outside surface—between Turkey Red, Plate 721/1, page 94 (W) and Turkey Red, Plate 721/3, page 94 (W) with veins near Currant Red, Plate 821/3, page 167 (W); inside surface—between Turkey Red, Plate 721/1, page 94 (W) and Turkey Red, Plate 721/3, page 94 (W) with veins near Currant Red, Plate 821/3, page 167 (W).

*General color effect.*—Newly opened flower—near Turkey Red, Plate 721, page 94 (W). 2–3 days open flower—between Turkey Red, Plate 721/1, page 94 (W) and Turkey Red, Plate 721/3, page 94 (W).

*Behavior.*—Flowers persist on plant as they become old; when flower is pulled off, the stamens and petals come off as a unit, leaving only the pistil adhering to the receptacle.

*Longevity.*—On bush in garden from 4 to 7 days during March. Cut flowers grown outdoors and kept at room temperature—from 3 to 5 days in March.

*Reproductive organs*

Stamens: Highly variable in number; from 10 to 60; the reduced number occurs when petaloids develop instead of stamens; the stamens and petaloids are usually united for part of their length and intermixed.

*Length.*—Commonly about 20 mm.; most with anthers.

*Color of filament.*—Near Dawn Pink, Plate 523/3, page 137 (W).

*Color of anthers.*—General effect of near Buttercup Yellow, Plate 5/1, page 5 (W).

Pistils: Usually one fused pistil with from 7 to 13 filaments of varying degrees of development and fusion, apparently non-functional.

*Length.*—Up to 20 mm.

*Color.*—Near Chartreuse Green, Plate 663/3, page 90 (W).

Seed pods: None observed.

I claim:

A new and distinct variety of camellia plant, substantially as herein shown and described, characterized particularly as to novelty by the unique combination of a vigorous, upright-spreading, rather moderately branched plant habit, with attractive, large dark green foliage having large and coarse marginal serrations, moderate floriferousness, with the flowers usually borne terminally, either singly or double and only occasionally laterally, very attractive flowers of medium size and having from 25 to 35 petals, plus from 5 to 10 petaloids, with the open flowers being rather globular, and the petals being arranged in a graceful irregular manner usually covering most of the stamens and substantially corresponding to a camellia flower form classification identified as a full peony form, a distinctive and attractive bright Turkey Red flower color, and a long blooming period ranging from late November or early December to April in southern California.

No references cited.

ABRAHAM G. STONE, *Primary Examiner.*